United States Patent
Thomas et al.

(10) Patent No.: US 6,620,380 B2
(45) Date of Patent: Sep. 16, 2003

(54) METHOD, DEVICE AND COMPOSITION FOR THE SUSTAINED RELEASE OF AN ANTIMICROBIAL GAS

(75) Inventors: John E. Thomas, River Falls, WI (US); Patrick H. Kilawee, Hugo, MN (US)

(73) Assignee: Ecolab, Inc., St. Paul, MN (US)

( * ) Notice: Subject to any disclaimer, the term of this patent is extended or adjusted under 35 U.S.C. 154(b) by 0 days.

(21) Appl. No.: 09/952,396

(22) Filed: Sep. 14, 2001

(65) Prior Publication Data

US 2003/0133833 A1 Jul. 17, 2003

(51) Int. Cl.[7] .................................................. A61L 9/00
(52) U.S. Cl. ................ 422/29; 252/187.21; 252/187.23; 422/3; 422/28; 422/37; 422/105; 422/116; 422/305; 423/477
(58) Field of Search ................................ 422/3, 28, 29, 422/37, 105, 108, 116, 305; 206/213.1; 423/477; 252/187.21, 187.23

(56) References Cited

U.S. PATENT DOCUMENTS

| | | | |
|---|---|---|---|
| 4,104,190 A | * 8/1978 | Hartshorn | 252/187.21 |
| 4,258,056 A | 3/1981 | Lentsch | 424/303 |
| 4,284,653 A | 8/1981 | Shigeoka et al. | 426/312 |
| 4,295,932 A | 10/1981 | Pocius | 162/161 |
| 4,297,224 A | 10/1981 | Macchiarolo et al. | 210/755 |
| 4,324,635 A | 4/1982 | Sweeney | 204/266 |
| 4,325,934 A | 4/1982 | Swindells et al. | 423/478 |
| 4,330,531 A | 5/1982 | Alliger | 424/149 |
| 4,370,305 A | 1/1983 | Affonso | 422/292 |
| 4,376,787 A | 3/1983 | Lentsch et al. | 424/315 |
| 4,460,373 A | 7/1984 | Beavan | 8/103 |
| 4,542,008 A | 9/1985 | Capuano et al. | 423/477 |
| 4,547,381 A | 10/1985 | Mason et al. | 426/316 |
| 4,585,482 A | 4/1986 | Tice et al. | 106/15.05 |
| 4,689,169 A | 8/1987 | Mason et al. | 252/186.24 |
| 4,832,972 A | 5/1989 | Toledo-Flores et al. | 426/327 |
| 4,908,188 A | 3/1990 | Jefferis, III et al. | 422/111 |
| 4,935,153 A | 6/1990 | Favstritsky et al. | 210/755 |
| 4,966,716 A | 10/1990 | Favstritsky et al. | 210/755 |
| 4,966,775 A | 10/1990 | Donofrio et al. | 424/661 |
| 5,091,107 A | 2/1992 | Hutchings | 252/187.21 |
| 5,208,057 A | 5/1993 | Greenley et al. | 426/332 |
| 5,229,072 A | 7/1993 | Tarancon | 422/37 |
| 5,289,691 A | 3/1994 | Schlosser et al. | 62/78 |
| 5,360,609 A | 11/1994 | Wellinghoff | 514/772.3 |
| 5,382,520 A | 1/1995 | Jenson et al. | 436/55 |
| 5,408,834 A | 4/1995 | Schlosser et al. | 62/78 |
| 5,476,579 A | 12/1995 | Choi et al. | 204/95 |
| 5,631,300 A | 5/1997 | Wellinghoff | 514/772.3 |
| 5,639,295 A | 6/1997 | Wellinghoff et al. | 106/15.05 |
| 5,639,559 A | 6/1997 | Mason et al. | 423/472 |
| 5,650,446 A | 7/1997 | Wellinghoff et al. | 514/772.3 |
| 5,695,814 A | 12/1997 | Wellinghoff et al. | 427/213 |
| 5,705,050 A | 1/1998 | Sampson et al. | 205/687 |
| 5,705,092 A | 1/1998 | Wellinghoff et al. | 252/187.21 |
| 5,707,739 A | 1/1998 | Wellinghoff et al. | 428/403 |
| 5,736,016 A | 4/1998 | Allen | 203/327 |
| 5,788,687 A | 8/1998 | Batich et al. | 604/890.1 |
| 5,853,689 A | 12/1998 | Klatte | 423/478 |
| RE36,064 E | * 1/1999 | Davidson et al. | 424/665 |
| 5,888,528 A | 3/1999 | Wellinghoff et al. | 424/405 |
| 5,914,120 A | 6/1999 | Wellinghoff et al. | 424/406 |
| 5,922,776 A | 7/1999 | Wellinghoff et al. | 514/772.3 |
| 5,965,264 A | 10/1999 | Barenberg et al. | 428/402 |
| 5,967,202 A | 10/1999 | Mullen et al. | 141/104 |
| 5,974,810 A | 11/1999 | Speronello | 62/66 |
| 5,980,826 A | 11/1999 | Barenberg et al. | 422/37 |
| 5,984,993 A | 11/1999 | Mainz et al. | 71/12 |

(List continued on next page.)

*Primary Examiner*—Krisanne Thornton
(74) *Attorney, Agent, or Firm*—Vidas, Arrett & Steinkraus

(57) ABSTRACT

A unitary container housing having a plurality of sealed compartments each containing a dry composition which will gradually release an antimicrobially active gas upon exposure to moist air, and each compartment being separately openable to expose its contents to the environment, and a method of using the same.

20 Claims, 2 Drawing Sheets

U.S. PATENT DOCUMENTS

| | | | |
|---|---|---|---|
| 6,004,439 A | 12/1999 | Bakhir et al. | 204/260 |
| 6,046,243 A | 4/2000 | Wellinghoff et al. | 514/772.3 |
| 6,071,483 A | 6/2000 | Pastore | 422/255 |
| 6,071,539 A | 6/2000 | Robinson et al. | 424/466 |
| 6,077,495 A | 6/2000 | Speronello et al. | 423/477 |
| 6,171,558 B1 | 1/2001 | Simpson | 422/186.3 |
| 6,238,643 B1 | 5/2001 | Thangaraj et al. | 423/477 |
| 6,269,946 B1 * | 8/2001 | Colombo | 206/213.1 |

* cited by examiner

METHOD, DEVICE AND COMPOSITION FOR THE SUSTAINED RELEASE OF AN ANTIMICROBIAL GAS

FIELD OF THE INVENTION

The present invention relates to a method and device for the controlled and sustained release of chlorine dioxide gas.

BACKGROUND OF THE INVENTION

Chlorine dioxide in low concentrations, i.e. up to 1,000 ppm, has long been recognized as useful as an antimicrobial and as a deodorant. In the presence of relatively low concentrations of chlorine dioxide, odiferous chemicals are oxidized to compounds which have essentially no odor. Such compounds include, for example, aldehydes, amines and thiols which are oxidized respectively to alcohols or acids, nitro compounds or various intermediates such as nitroso compounds, and to disulfides or oxides of sulfur. At higher levels than required for deodorizing, chlorine dioxide may act as an antimicrobial.

Its use is particularly advantageous for use where it is desirable to reduce the antimicrobial population and reduce noxious odors on and around foodstuffs for several reasons. First of all, chlorine dioxide generation does not result in the noxious byproducts such as chloramines or chlorinated organic compounds that can be produced when elemental chlorine is utilized for the same or similar purposes. Secondly, it chlorine dioxide gas is also generally considered to be safe for human contact at concentrations considered to be effective for deodorization and most antimicrobial applications because such concentrations are generally low.

There are several methods which have been suggested for generation of chlorine dioxide. One method is to use a solid mixture of a metal chlorite and an acid in a liquid, aqueous environment. A second method combines a metal chlorite and a solid acid where chlorine dioxide gas is released under dry conditions. A third system employs the combination of a metal chlorite and a solid organic anhydride to generate a high concentrated flow of chlorine dioxide which must be diluted with a constantly flowing stream of inert gas.

Such solid reagent systems, however, have a couple of disadvantages. Typically, upon mixing there is a sudden, highly concentrated stream of chlorine dioxide generated, and the mixture of reactants, if not properly contained and kept moisture free, produce chlorine dioxide prematurely reducing the shelf life of the reactants.

Methods for the controlled release of chlorine dioxide gas have been developed for purposes of both deodorization and for reduction of microbial populations.

For instance, U.S. Pat. No. 6,238,643 describes a method of producing an aqueous solution of chlorine dioxide from the reaction of a metal chlorite and an acid forming component which do not react to produce chlorine dioxide in the substantial absence of water. The reactants are separated from liquid water by a membrane which allows the controlled passage of liquid water and/or water vapor into contact with the reactants. The chlorine dioxide thus generated passes out through the membrane into the liquid water to produce the desired aqueous solution.

U.S. Pat. No. 6,077,495 describes a method, composition and system for generating chlorine dioxide gas in a controlled release manner by combining at least one metal chlorite and a dry solid hydrophilic material that reacts with the metal chlorite in the presence of water vapor, but does not react with the metal chlorite in the substantial absence of liquid water or water vapor to produce chlorine dioxide gas in a sustained amount of from about 0.001 to 1,000 ppm.

U.S. Pat. No. 5,091,107 describes methods and devices for the production of controlled quantities of chlorine dioxide at concentrations which are effective to function as a deodorant or a germicide whereby aqueous chlorite compositions such as aqueous sodium chlorite are brought into contact at a controlled rate through capillary means, e.g. a wick with an absorbent pad containing acid or other reactant which will react with the chlorite and form chlorine dioxide.

However, in each of the above described methods, it is still difficult to maintain a sustained release of chlorine dioxide over a period of time.

SUMMARY OF THE INVENTION

The present invention relates to a method, composition and device for the controlled and sustained release of chlorine dioxide over a period of time.

More specifically, the present invention relates to a method of generating an antimicrobially active gas including the steps of providing a dry solid composition which reacts in the presence of water or water vapor to the gas, but does not react in the absence of water or water vapor, and exposing the composition to a moist environment.

The composition is divided into a plurality of separate portions, each of which is contained in a separate sealed compartment of a unitary container housing. The sealed compartments are sequentially unsealed to expose the contents to the environment around the container housing in response to a predetermined stimulus event.

The release of the gas can be controlled and sustained using the method, composition and device of the present invention.

The present invention, in another embodiment relates to a device for the generation of an antimicrobially active gas including a unitary container housing having a plurality of sealed compartments each of which contains a composition which will gradually release chlorine dioxide upon exposure to moist air, a compartment opener operable on the unitary container housing to open a compartment in sequence in response to an opening signal and a controller operable to periodically issue a opening signal to the opener.

The reactants may be in solid form. If it is in solid form, only a single compartment is required. The reactants may also be in liquid form, or one reactant may be a liquid and one reactant a solid. If at least one reactant is in liquid form, a barrier may be provided between the reactants, thus requiring two compartments be opened in order to allow the reactants to mix.

In one embodiment, the present invention relates to a device and method for the controlled and sustained release of an antimicrobially active gas including a power supply, an electrical switch, a plurality of conductors, a controller and a container having a top and bottom and housing a plurality of sealed pockets. Each pocket contains the gas generating composition of the present invention. The conductors are connected to the electrical switch and each terminate in an electrode. Each electrode is attached to a sealed pocket. The controller is operatively connected to the power supply and to the electrical switch, and is capable of directing the switch to apply power sequentially to each conductor for a first predetermined time interval. There is a second predetermined time interval between each application of power to each conductor.

Using the device as described above allows for sequentially supplying power to each of the conductors for a first predetermined time interval such that the sealed pockets may be opened sequentially. There is a second predetermined time interval between each application of power to each conductor.

Upon application of power to the conductors and thus to each electrode, the sealed pockets open, exposing the contents to atmospheric moisture thereby initiating the gas generating reaction.

DETAILED DESCRIPTIONS OF THE PREFERRED EMBODIMENTS

The present invention is directed to a method, composition and device for the controlled and sustained release of a deodorizing and/or antimicrobially active gas over a period of time. The reactants and device of the present invention are designed such that the release of the gas is accomplished at a rate which results in low concentrations of the gas being released over an extended period of time. The rate and duration of the release of gas may be controlled using the composition and device of the present invention. This is controlled by controlling the exposure rate of a chemical composition to conditions which trigger the reaction which produces the gas, such as ambient moisture.

Figure 1:
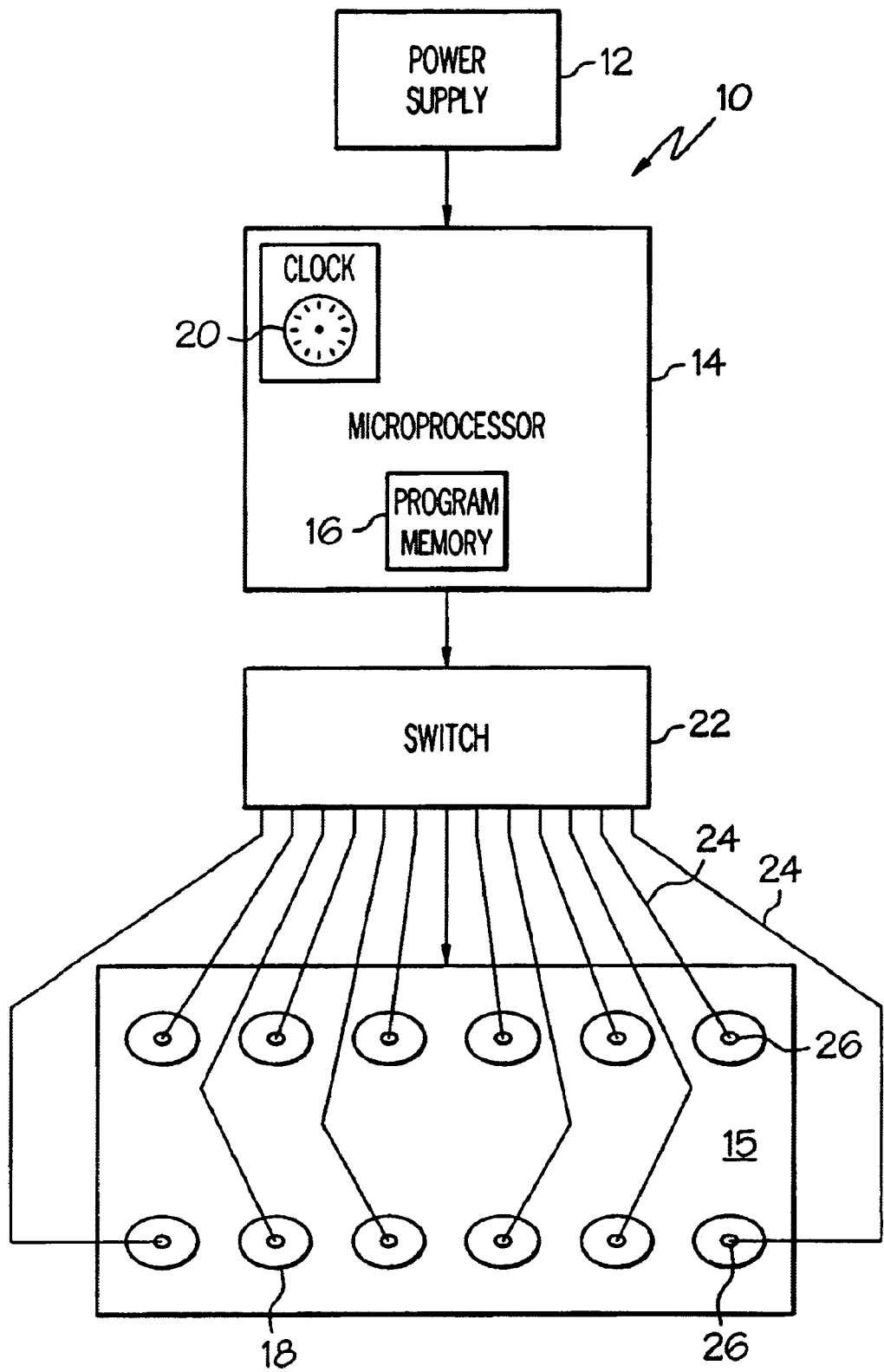
FIG. 1 is a schematic of one embodiment of the device of the present invention.
Figure 2:
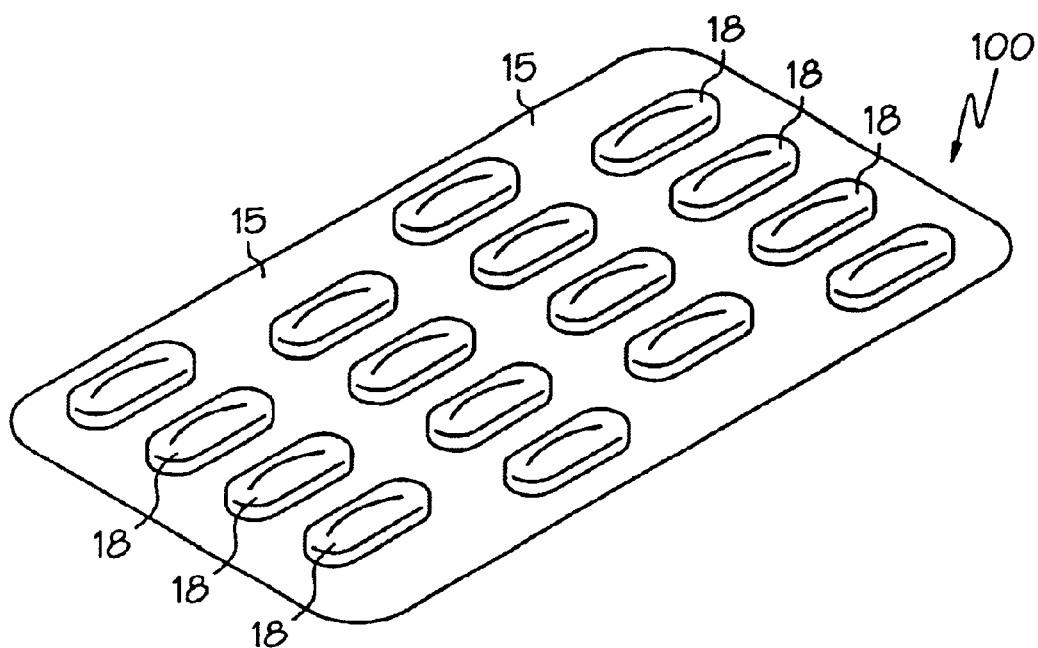
FIG. 2 illustrates one embodiment of a container which may be used in the present invention.
Figure 3:
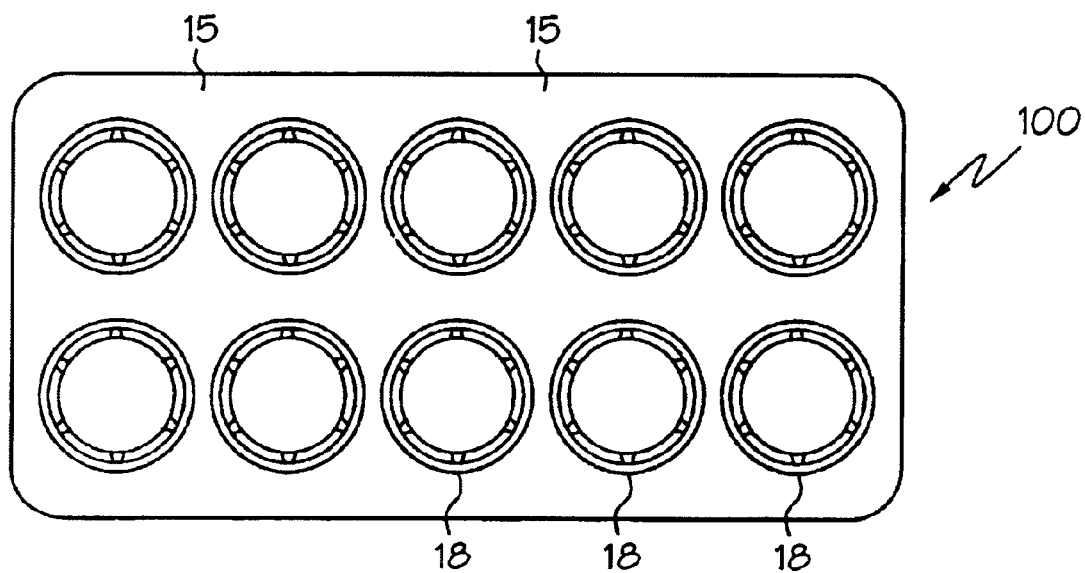
FIG. 3 illustrates an alternative embodiment of the container which may be used with the device of the present invention.

FIG. 1 shows generally at 10, a schematic diagram illustrating one embodiment of the device of the present invention. The device has a container 15 having a plurality of pockets 18. In this embodiment container 15 is shown with a 12-pocket configuration. The container may house any number of pockets from one on up. Preferably, the container will house between about 4 and 30 pockets. FIGS. 2 and 3 show alternative embodiments of the container of the present invention having 16 and 10 pockets consecutively. Such containers may have anywhere from one pocket on up. Suitably, the number of pockets may be between about 4 and 30, but the invention is not limited as such.

The term pocket may also be hereinafter used interchangeably with compartment, reservoir, recess, cell, cup, dish, cavity, and the like, only to mention a few.

FIGS. 2 and 3 show a unitary container 15 having a series of individual pockets 18, each of which holds the composition of the present invention. The containers 15 suitable for use herein may be, for example, configured similarly to an egg carton, ice cube tray, or the like. This invention is not limited in scope to any particular type of packaging or container which may be used in accordance herewith providing that the packaging or container is suitable for use with the device herein. Any type of package or container capable of being made to protect the composition of the present invention from the environment, in particular moisture, may find utility herein. There is an endless array of packaging and one of ordinary skill in the art would understand that the configuration, materials, and so forth of the container may be easily changed without departing from the scope of the present invention. The container or package should be configured such that it may be sealed in such a manner that the contents are protected from exposure to the environment, in particular, contact with moisture is prevented.

The container suitable for use with the device described herein is generally formed from one or more materials that can be shaped and sealed to form at least one pocket which holds the gas generating composition of the present invention, and a top for sealing the composition in the pocket. Suitably, the base or bottom of the container 15 has a plurality of pockets for holding the composition of the present invention.

One specific type of package which may find utility herein is a "blister pack", a term of art known to those of ordinary skill. A blister pack system is typically described as a blister to which a lid or backing of the same or a different material may be tightly fitted and sealed near the outer perimeters of the blister and or lid, and by virtue of the outer perimeters of the blister and lid being continuously sealed to the backing material. The sealed blister prevents outside moisture in the form of vapor from coming into contact with the composition of the present invention. Examples of this type of packaging suitable for use herein may be found in U.S. Pat. No. 5,803,248 and U.S. Pat. No. 6,006,913, both of which are incorporated by reference herein in its entirety.

Within each pocket or "blister" is the composition of the present invention. The pocket may contain any amount of composition suitable for the particular use to which it is being put. However, for many applications, an amount of about 1 g to about 100 g in each pocket or blister will be sufficient. However, for other applications, gallon size containers, drums, and so forth may be used depending on the size of the operation.

The package or container useful herein may include a lower part having a cavity defining a composition holding receptacle, i.e. pocket 18, the composition being disposed within the receptacle, and a covering material which covers the cavity thereby enclosing the product in the container in such a way that it is impermeable to water or water vapor.

The bottom member or backing and the covering material of the container may be made of the same or of a different material. In this embodiment, the top material may be any material which may be opened through the use of an electrical current that generates heat by building of resistance in an electrode, or by heat, such as by heating a wire. Suitably, in this embodiment, the top is in the form of a film or the like which is capable of being melted upon application of an energy source such as an electric current or heat. Suitably, the top is in the form of a thin film or laminate that is comprised of a polymeric material. The laminate has at least a first layer and a second layer, but may have more layers as well.

The polymeric material suitable for use herein may be any polymeric material known for use in film or laminate form such as polyolefins including polyethylene and polypropylene and copolymers and terpolymers thereof, ethylene and propylene alpha olefin copolymers and terpolymers, polyesters such as MYLAR®, cellophane, SARAN®, and so forth.

The base or bottom of the container may be manufactured of any material that is or can be made impermeable to water or water vapor including polymeric materials, laminates or composites including those having polymeric materials, paper products such as cardboard, and so forth by molding. Paper products may require further treatment, lamination, a coating, or similar for providing a moisture-proof barrier. The bottom portion of the container may be polymeric in nature. Examples of materials suitable for use include polyolefins such as low density polyethylene (LDPE), high density polyethylene (HDPE) and polypropylene, polystyrene, and so forth. The container base may be made by thermoforming, molding, extrusion, and so forth. Metals such as an aluminum may also find utility herein but they may tend to be corrosive.

To enclose the product in such a way that it is sufficiently impermeable to water or water vapor, the covering or top may be sealed to the container 15 in such a way that each individual pocket 18 is sealed. Preferably, the covering material is in the form of a film or laminate (not shown) wherein a single piece covers and seals all of the pockets 18. The film or laminate may be in whole or in part made of polymeric materials. If it is in the form of a laminate, it may also include a foil-type of material, for instance. The seal may be formed by heat sealing or adhesively, for example. Any method known to those of skill in the art for providing an adequate seal may find utility herein. The method of sealing should provide a moisture-proof barrier thus protecting the composition within the pocket from premature exposure to ambient moisture.

Each individual pocket 18 may be sequentially unsealed to expose the contents to ambient moisture to initiate the gas forming reaction. This may be accomplished through the use of an electrical circuit having a series of conductors 24 and electrodes 26, each conductor 24 terminating at an individual pocket 18. A conductor 24 runs from an electrical switch box 22 or similar device to the center of each pocket 18 and terminates in an electrode 26. The conductor may be in the form of a wire such as a 20-gauge wire. Higher gauge wires may be used, as well as lower gauge wires. However, wires having a smaller diameter, i.e. higher gauges, may have more of a tendency to break with heat. An electrical charge may be sent to each individual electrode 26 at a different time. Each conductor 24 is terminated with an electrode 26. Electrode 26 is in contact with the material covering each pocket 18.

If one reactant is a liquid, and a barrier (not shown) is provided between reactants in each pocket 18, then two electrodes 26 may be provided to each pocket, one which may open the pocket 18 itself, and one which would open the barrier, allowing the reactants to intermix. In this embodiment, either one or two conductors 24 may be provided to each pocket. If two conductors 24 are provided, then an electrical charge may be sent to each.electrode 26 at substantially the same time. If one conductor 24 is provided, it may branch at the end into two conductors 24. In this instance, a single electrical charge would be required to open both the pocket 18 and the barrier.

If the covering material is in the form of a film, it may be attached to the film. If the covering material is in the form of a laminate, electrode 26 may be sandwiched in between the layers of the laminate. Alternatively, electrode 26 may be sandwiched in between the covering material (not shown) and the bottom part of container 15 where the seal is formed. Resistance is created in the electrode 26 at the termination of each conductor 24. The resistance thus created causes the conductor 24 to heat up and melt the film or laminate thus opening pocket 18 and exposing the contents to the atmosphere.

The resistance created at the terminal end in each cell causes the wire to heat up, thereby melting the polymeric film or laminate. The contents are exposed to ambient moisture, thus starting the reaction to release chlorine dioxide.

Switch 22, in this embodiment, is in turn in communication with a microprocessor 14 which is in turn connected to a power supply 12 which may be in the form of a DC or an AC power source including a 24VAC power supply or a 9-volt battery, for instance. Microprocessor 14 may have program memory 16 as well as a timing device 20. The timing device 20 in this embodiment 20 is shown in the form of a real time clock, but may be in the form of a counter, or other timing device. Microprocessor 14 may be further equipped with a reset button (not shown) to be used when the entire contents of all of the pockets 18 have been spent and the container 15 may be changed.

At periodic intervals, the microprocessor 14 directs electricity to a each conductor 24 in sequence. The time interval will ordinarily depend on the length of time for the reactants of each pocket 18 to be used. The microprocessor 14 may also be connected to a timing device and/or to a monitor capable of detecting the concentration of gas. The monitor may produce a signal that will indicate when the reaction in the compartment is spent, or when chlorine dioxide concentration is too low, and thus when the next compartment should be unsealed.

The device may also include a monitor and signal for change out of the container itself to notify the use when the entire container requires changing. The signal may be in the form of an alarm or LED, for instance.

The device as described above allows each pocket or cell to be opened in series. In this manner, the device provides for a longer term method of releasing antimicrobial and/or deodorizing gas.

Alternatively, the device may have an on/off switch to allow for manual operation. In this embodiment, the switch box 22 may also be connected to a monitor having a signal such as an LED set to the timing device 20 that will indicate when the reaction in the compartment is spent, and thus when the next compartment should be unsealed.

The description and figures above are intended as exemplary of the present invention only, and are not intended to limit the spirit and scope of the present invention.

Any composition capable of producing an antimicrobially active gas may be utilized in the device and method of the present invention. Most conveniently, this is accomplished by exposing the composition to liquid water or water in vapor form. Such generation of gas is desirably accomplished in a controlled release manner in amounts effective to reduce microbial populations including mold, yeast, fungi, and other microbes. In some instances, the gas may also act as a deodorant thereby reducing offensive and noxious fumes.

Examples of gases that may suitably be generated in the presence of water or water vapor in this fashion include, but are not limited to, chlorine dioxide, halogens including chlorine, bromine and iodine, ozone, ethylene oxide, or other vapor emitting corrosion inhibitors.

Suitably, the compositions useful herein are solid. However, the reactants in a liquid form may also be used. The composition of the present invention includes at least one metal chlorite and at least one material which is capable of reacting with the metal chlorite to form chlorine dioxide in the presence of water or water vapor.

The metal chlorites employed in the present invention can generally be any metal chlorite. Suitably, the metal chlorites are alkali metal chlorites, such as sodium chlorite and potassium chlorite. Alkaline earth metal chlorites can also be employed. Examples of alkaline earth metal chlorites include barium chlorite, calcium chlorite, and magnesium chlorite. Most suitably, the metal chlorite is sodium chlorite.

The material for reacting with the metal chlorite is suitably a dry hydrophilic material as described in U.S. Pat. No. 6,077,495 incorporated by reference herein in its entirety. Examples of such dry solid hydrophilic materials suitable for reacting with the metal chlorites include, but are not limited to, synthetic zeolites, such as A, X, Y, and mordenite; natural zeolites such as chabazite and clinoptilolite; hydrous clays, such as bentonite, kaolin, attapulgite and halloysite; calcined clays, such as metakaolin, spinel phase kaolin, calcined bentonite, calcined halloysite, and calcined attapulgite; acidified synthetic zeolites, such as A, X, Y, and mordenite that have been contacted with one or more acidic solutions containing sulfuric acid, hydrochloric acid, nitric acid, or other acidic compound (e.g. calcium chloride) so that the pH of the resulting aqueous phase of the mixture is below 10.5; acidified natural zeolites such as chabazite and clinoptilolite; acidified clays, such as bentonite, kaolin, attapulgite and halloysite that have been contacted with one or more acidic solutions containing sulfuric acid, hydrochloric acid, nitric acid, or other acidic compounds (e.g. lanthanum chloride) so that the pH of the resulting aqueous phase of the mixture is below 10.5; acidified calcined clays, such as metakaolin, spinel phase kaolin, calcined bentonite, calcined halloysite, and calcined attapulgite that have been contacted with one or more acidic solutions containing sulfuric acid, hydrochloric acid, nitric acid, or other acidic compounds (e.g. acetic acid) so that the pH of the resulting aqueous phase of the mixture is below 10.5; salts, such as aluminum sulfate, magnesium sulfate, calcium carbonate, and particularly deliquescent acidic salts, such as calcium chloride, magnesium chloride, lithium chloride, and magnesium nitrate; solid acids, such as boric acid, tartaric acid and citric acid; organic acid anhydrides such as phthalic anhydride, maleic anhydride, succinic anhydride and glutaric anhydride; and mixtures thereof.

In one embodiment, the reactants acidified calcined metakaolin clay and sodium chlorite, both of which are in solid form.

The amount of reactants utilized may suitably be between 50 and 100 g with sodium chlorite being about 5 wt-% of the composition and the acidified clay being about 95 wt-% of the composition. In this embodiment, the device includes a plurality of sections or pouches separated from one another, each of which comprises 50 g to 100 g of reactants. As shown in FIG. 2, the device may be a 12-pocket pack.

Chlorine dioxide delivery in a suitable embodiment maybe about 1–2 ppm in the first several hours, about 0.5 to 1.0 ppm ($t_{1/2}$) after about 24 hours, and levels off to about 0.1 ppm shortly thereafter. The circuit is set with a timing device such that the next pouch may be activated daily, every other day, every few days, on a weekly basis, and so forth.

At the time of use, the mixture is exposed to atmospheric water vapor resulting in the production of chlorine dioxide gas at a sustained concentration of about 0.025 to about 1000 ppm. The generation of chlorine dioxide using such methods are described, for example, in U.S. Pat. No. 4,547,381, U.S. Pat. No. 4,585,482, U.S. Pat. No. 5,974,810, U.S. Pat. No. 6,077,495, U.S. Pat. No. 5,650,446, U.S. Pat. No. 5,695,814, U.S. Pat. No. 5,707,739, U.S. Pat. No. 5,091,107, U.S. Pat. No. 5,888,528, U.S. Pat. No. 5,922,776, U.S. Pat. No. 5,965,264, U.S. Pat. No. 5,980,826, U.S. Pat. No. 6,046,243, and so forth, all of which are incorporated by reference herein in their entirety.

If transient high concentrations of chlorine dioxide gas in undesirable, an inert gas stream can be used to reduce the concentration of chlorine dioxide gas in the atmosphere.

The mixture of metal chlorite, an acidic material, and any other desired additives may be packaged for shipment and storage in containers made of materials which are resistant to the passage of liquid water and water vapor. Examples of such materials include metal cans, glass jars, foil pouches, and barrier layer polymer laminates. Alternatively, a self-contained composition for the generation of gas may be utilized in the present invention wherein a shrink-wrapped container is equipped with a battery such as a 9-volt battery, and a circuit. A charge causes the wire to heat and melt the shrink wrap thereby exposing the chemicals to the moisture in the ambient air. The battery may be further equipped with a timing device.

The rate at which chlorine dioxide is generated will, to a certain extent, depend on the relative humidity of the environment in which the reactants are placed. For instance, the method of the present invention can be conducted under low humidity conditions (e.g. 10% relative humidity) up to 100% high humidity conditions. As previously indicated, the amount of chlorine dioxide gas generated per given amount of the mixture will depend, in part, on the relative humidity of the surrounding atmosphere. In general, higher humidity will result in a higher concentration of chlorine dioxide gas.

The present invention may be utilized in any application where it is desirable to deodorize, or where it is desirable to reduce the population of microbes present including fungi, molds, yeast, slimes, bacteria, and so forth, other microbiological growths, and so forth. Using the present invention, the amount of chlorine dioxide generated may vary from anywhere between about 0.01 to about 1,000 ppm, with deodorizing typically occurring at the lower end of the concentration range of as little as 100 ppm or less. See for example, U.S. Pat. No. 5,974,810 incorporated by reference herein in its entirety.

The device and method of the present invention for the generation of antimicrobial gases may be used to treat liquids, solids, and gaseous environments. The device, method and composition of the present invention may be utilized in any application where deodorization is desirable.

Examples of gaseous environments which may be treated include those containing noxious and/or objectionable gases such as animal environments, smoke-laden environments (e.g. tobacco smoke) such as nightclubs, exhaust systems from noxious gas producing facilities (e.g. chemical plants), and so forth.

The present invention is particularly suitable for the treatment of environments on and around foodstuffs including processing plants, storage lockers, transportation vehicles and so forth.

Further environments in which the present invention may be utilized include refrigeration units including ice and beverage machines, gym lockers, vacation homes, bathroom stalls, cleaning equipment/supply lockers, lockers in gyms, garbage receptacles, closets, and so forth.

One of ordinary skill in the art would understand that the embodiments described above are by way of exemplification and are not intended to limit the scope of the present invention.

What is claimed is:

1. A method of generating chlorine dioxide gas comprising:
   providing a dry solid composition which reacts in the presence of water or water vapor to produce an antimicrobially active gas, but does not react in the absence of water or water vapor, and
   exposing the composition to a moist environment, wherein the composition is divided into a plurality of separate portions, each contained in a separate sealed compartment of a container housing, and the sealed compartments are sequentially unsealed to expose the contents thereof to the environment around said container housing in response to a predetermined stimulus event.

2. The method of claim 1 wherein said gas is chlorine dioxide, a halogen, ozone or ethylene oxide.

3. The method of claim 1 wherein said stimulus event is a time increment.

4. The method of claim 1 wherein said stimulus event is a monitor signal indicative of a depleted concentration of gas.

5. The method of claim 1 wherein said sealed compartments are unsealed by an electrical current.

6. A device for delivering an antimicrobially active gas comprising a unitary container housing having a plurality of sealed compartments each containing a dry composition which will gradually release chlorine dioxide upon exposure to moist air, a compartment opener operable on said unitary container housing to open a said compartment in sequence in response to an opening signal and a controller operable to periodically issue a opening signal to the opener.

7. The device of claim 6 wherein said controller issues an opening signal in response to a timing program.

8. The device of claim 6 further comprising a monitor of gas concentration and said controller is configured to issue a said opening signal in response to a depleted concentration of gas indication received from said monitor.

9. The device of claim 6 wherein each of the compartments is sealed by a thermoplastic film cover, and said compartment opener comprises a heating unit adapted to melt said film cover in response to an opening signal.

10. A unitary container housing having a plurality of sealed compartments each containing a dry composition which will gradually release chlorine dioxide upon exposure to moist air, and each compartment being separately openable to expose its contents to the environment.

11. A container housing as in claim 10 wherein each of the compartments is sealed by a thermoplastic film cover.

12. A device for the sustained release of an antimicrobially active gas comprising:

a) a power supply;

b) an electrical switch;

c) a plurality of conductors connected to said electrical switch each of which terminates in an electrode;

d) a controller operatively connected to said power supply and said electrical switch; and e) a container having a top and a bottom housing a plurality of sealed pockets, each pocket containing a composition which generates an antimicrobially active gas upon exposure to water or water vapor and wherein each electrode is attached to a pocket;

wherein the controller directs the switch to apply power sequentially to each conductor for a first predetermined time interval with a second predetermined time interval between each application of power for opening said sealed pockets.

13. The device of claim 12 wherein said top is film or a film laminate having at least a first layer and a second layer.

14. The device of claim 12 wherein said electrode increases in temperature upon application of power to said conductor to a temperature sufficient to melt said film or laminate.

15. The device of claim 13 wherein said electrode is attached to said sealed pocket between said first and said second layer of said film laminate.

16. The device of claim 12 wherein said gas is chlorine dioxide, a halogen, ozone or ethylene oxide.

17. The device of claim 12 wherein said composition in said each pocket comprises a metal chlorite and an acidic component.

18. The device of claim 12 wherein said power supply is a 9-volt battery or a 24VAC power source.

19. The device of claim 12 wherein said conductor is a wire of between about 12-gauge and about 30-gauge.

20. A method for the sustained release of an antimicrobially active gas comprising the steps of:

a) providing a container having a plurality of sealed pockets each of which contains a composition which generates an antimicrobially active gas upon exposure to water or water vapor, a plurality of conductors terminated in an electrode and each electrode attached to at least one of said plurality of said sealed pockets, an electrical switch connected to said conductors which is in turn connected to a power source; and b) sequentially supplying power to each of said conductors for a first predetermined time interval with a second predetermined time interval between each application of power for opening said sealed pockets.

* * * * *